(12) United States Patent
Chen et al.

(10) Patent No.: US 6,528,449 B1
(45) Date of Patent: Mar. 4, 2003

(54) THREE COORDINATE ALUMINUM CATALYST ACTIVATOR COMPOSITION

(75) Inventors: Eugene Y. Chen, Midland, MI (US); William J. Kruper, Jr., Sanford, MI (US); Gordon R. Roof, Midland, MI (US); David J. Schwartz, Lake Jackson, TX (US); Joey W. Storer, Plymouth, MN (US)

(73) Assignee: The Dow Chemical Comapny, Midland, MI (US)

( * ) Notice: Subject to any disclaimer, the term of this patent is extended or adjusted under 35 U.S.C. 154(b) by 122 days.

(21) Appl. No.: 09/702,442

(22) Filed: Oct. 31, 2000

Related U.S. Application Data

(62) Division of application No. 09/330,671, filed on Jun. 11, 1999, now Pat. No. 6,187,940.
(60) Provisional application No. 60/096,801, filed on Aug. 17, 1998, and provisional application No. 60/100,487, filed on Sep. 16, 1998.

(51) Int. Cl.$^7$ .................................. B01J 31/14
(52) U.S. Cl. .................. 502/152; 502/153; 502/154; 502/171; 556/27; 556/51; 556/52; 556/53
(58) Field of Search ................ 526/943, 170, 526/161, 160, 348; 502/703

(56) References Cited

U.S. PATENT DOCUMENTS

| | | | | |
|---|---|---|---|---|
| 5,453,410 | A | 9/1995 | Kolthammer et al. | 502/155 |
| 5,470,993 | A | 11/1995 | Devore et al. | 556/11 |
| 5,527,929 | A | 6/1996 | Timmers et al. | 556/7 |
| 5,556,928 | A | 9/1996 | Devore et al. | 526/127 |
| 5,602,269 | A | * 2/1997 | Biagini et al. | 556/170 |
| 5,616,664 | A | 4/1997 | Timmers et al. | 526/127 |
| 5,624,878 | A | 4/1997 | Devore et al. | 502/152 |
| 5,854,166 | A | * 12/1998 | Marks et al. | 502/153 |
| 5,895,771 | A | * 4/1999 | Epstein et al. | 502/103 |
| 6,187,940 | B1 | * 2/2001 | Chen et al. | 556/176 |
| 6,211,111 | B1 | * 4/2001 | Chen et al. | 502/152 |
| 6,214,760 | B1 | * 4/2001 | Chen et al. | 502/103 |
| 6,291,614 | B1 | * 9/2001 | Chen et al. | 526/151 |

FOREIGN PATENT DOCUMENTS

| | | | | |
|---|---|---|---|---|
| WO | WO 97/27228 A1 | * 7/1997 | | C08F/10/00 |
| WO | WO 98/03558 A1 | * 1/1998 | | C08F/4/642 |

OTHER PUBLICATIONS

Chen, Y.–X.; Stern, C. L.; Marks, T. J. J. Am. Chem. Soc. 1997, 119, 2582.*
Chen, Y.–X.; Metz, M. V.; Li, L., Stern, C. L., Marks, T. J. J. Am. Chem. Soc. 1998, 120, 6287.*
Bochmann, M.; Sarsfield, M. J. Organometallics 1998, 17, 5908.*
Ewen, *Stud, In Surf. Sci. Catal.*, 89, 405–410, (1994).
Bochmann et al., (ACS Dallas Meeting, Mar. 1998, ABS. No. INOR 264, subsequently published, *Organometallics*, 1998, 17, 5908–5912),

* cited by examiner

*Primary Examiner*—David W. Wu
*Assistant Examiner*—Rip A. Lee

(57) ABSTRACT

Catalyst compositions useful for olefin polymerizations comprising a Group 3–10 metal complex and a compound corresponding to the formula: $AlAr^fQ^1Q^2$, or a dimer, adduct, or mixture thereof and further mixtures with aluminum compounds of the formula $AlAr^f_3$, where:

$Ar^f$ is a fluorinated aromatic hydrocarbyl moiety of from 6 to 30 carbon atoms;

$Q^1$ is $Ar^f$ or a $C_{1-20}$ hydrocarbyl group, optionally substituted with one or more cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally, such substituents may be covalently linked with each other to form one or more fused rings or ring systems; and $Q^2$ is an aryloxy, arylsulfide or di(hydrocarbyl)amido group, optionally substituted with one or more hydrocarbyl, cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally such substituents may be covalently linked with each other to form one or more fused rings or ring systems, said $Q^2$ having from 3 to 20 atoms other than hydrogen are useful as activators for olefin polymerizations.

8 Claims, No Drawings

THREE COORDINATE ALUMINUM CATALYST ACTIVATOR COMPOSITION

CROSS-REFERENCE TO RELATED APPLICATION

This application is a divisional from U.S. application Ser. No. 09/330,671, filed Jun. 11, 1999, now U.S. Pat. No. 6,187,940 which claims benefit from provisional applications No. 60/096,801, filed Aug. 17,1998, and No. 60/100,487, filed Sept. 16, 1998.

BACKGROUND OF THE INVENTION

The present invention relates to compositions that are useful as catalyst activators for olefin polymerizations. More particularly the present invention relates to such compositions that are particularly adapted for use in the coordination polymerization of unsaturated compounds having improved activation efficiency and performance. Such compositions are particularly advantageous for use in a polymerization process wherein catalyst, catalyst activator, and at least one polymerizable monomer are combined under polymerization conditions to form a polymeric product.

It is previously known in the art to activate Ziegler-Natta polymerization catalysts, particularly such catalysts comprising Group 3–10 metal complexes containing delocalized π-bonded ligand groups, by the use of an activator. Generally in the absence of such an activator compound, also referred to as a cocatalyst, little or no polymerization activity is observed.

A class of suitable activators are Lewis acids, especially alumoxanes, which are generally believed to be oligomeric or polymeric alkylaluminoxy compounds, including cyclic oligomers. Examples of alumoxanes (also known as aluminoxanes) include methylalumoxane (MAO) made by hydrolysis of trimethylaluminum as well as modified methylalumoxane (MMAO), wherein a portion of the trimethylaluminum in the foregoing hydrolysis is replaced by a higher trialkylaluminum compound such as triisobutylaluminum. MMAO advantageously is more soluble in aliphatic solvents than is MAO.

Generally alumoxanes contain on average about 1.5 alkyl groups per aluminum atom, and are prepared by reaction of trialkylaluminum compounds or mixtures of compounds with water (Reddy et al, *Prog. Poly. Sci.,* 1995, 20, 309–367). The resulting product is in fact a mixture of various substituted aluminum compounds including especially, trialkylaluminum compounds (resulting from incomplete reaction of the trialkylaluminum starting reagent or decomposition of the alumoxane). The amount of such free trialkylaluminum compound in the mixture generally varies from 1 to 50 percent by weight of the total product.

Although effective in forming an active olefin polymerization catalyst when combined with a variety of Group 3–10 metal complexes, especially Group 4 metal complexes, generally a large excess of alumoxane compared to metal complex, such as, molar ratios from 100:1 to 10,000:1, is required in order to produce adequate rates of polymerization. Unfortunately, the use of such large excesses of cocatalyst is expensive and also results in polymer having an elevated residual aluminum content as well as lower molecular weight. This former factor may adversely affect polymer properties, especially clarity and dielectric constant, whereas the latter issue relates to poor polymer performance.

Other types of monomeric aryloxyaluminum and arylamidoaluminum complexes have been found to be useful in metallocene catalyst activator packages, particularly as water and oxygenate scavengers. Examples include diisobutyl-2,6-di-t-butyl-4-methylphenoxyaluminum (DIBAL-BOT) as described in WO 97/27228 and Japanese kokai, 09-17629, or diisobutylhexamethyldisilylazayl aluminum (DIBAL-NS) as described by Rosen et al in WO 98/03558. Typically in such formulations, the Lewis acid, especially tris(pentafluorophanyl)borane, is first contacted with a metal complex to prepare the catalytically activated derivative. Thereafter, this derivative is generally not subject to ligand transfer with the aluminum compound.

A different type of activator compound is a Bronsted acid salt capable of transferring a proton to form a cationic derivative or other catalytically active derivative of such Group 3–10 metal complex, cationic charge transferring compounds, or cationic oxidizing activators, referred to collectively hereinafter as cationic activators. Preferred cationic activators are ammonium, sulfonium, phosphonium, oxonium, ferrocenium, silver, lead, carbonium or silylium compounds containing a cation/anion pair that is capable of rendering the Group 3–10 metal complex catalytically active. Preferred anions associated with this cation comprise fluorinated arylborate anions, more preferably, the tetrakis (pentafluorophenyl)borate anion. Additional suitable anions include sterically shielded, bridged diboron anions. Examples of such cationic activators are disclosed in U.S. Pat. Nos. 5,198,401, 5,132,380, 5,470,927, 5,153,157, 5,350,723, 5,189,192, 5,626,087 and in 5,447,895.

Further suitable activators for activating metal complexes for olefin polymerization include neutral Lewis acids such as tris(perfluorophenyl)borane and tris-(perfluorobiphenyl) borane. The former composition has been previously disclosed for the above stated end use in U.S. Pat. No. 5,721, 185, and elsewhere, whereas the latter composition is disclosed in Marks, et al, *J. Am. Chem. Soc.* 1996, 118, 12451–12452. Additional teachings of the foregoing activators may be found in Chen, et al, *J. Am. Chem. Soc.* 1997, 119, 2582–2583, Jia et al, *Organometallics,* 1997, 16, 842–857, and Coles et al, *J. Am. Chem. Soc.* 1997, 119, 8126–8126.

Tris(perfluorophenyl)aluminum is a strong Lewis acid as well. It has recently been prepared from the exchange of tris(perfluorophenyl)borane with trialkylaluminum, which gives a trialkylborane and tris-perfluorophenylaluminum, as described by Biagini et al U.S. Pat. No. 5,602,269. However, it generally performs poorly by itself as a catalyst activator compared with tris(perfluorophenyl)borane when used in an equimolar ratio with a metal complex. Similarly, It has further been demonstrated that active catalysts resulting from the use of an aluminate anion based upon tris-(perfluorophenyl)aluminum for the activation of ansa-metallocenes and biscyclopentadienyl derivatives of zirconium(IV) are generally of lower activity than those formed by the corresponding borane (Ewen, *Stud. in Surf. Sci. Catal.* 1994, 89, 405–410). A possible explanation for the poor performance of tris(perfluorophenyl)aluminum as an activator for metallocenes involving a back exchange reaction of a perfluorophenyl group has been proposed by Bochmann et al (ACS Dallas Meeting, March 1998, Abs. number INOR 264, subsequently published, *Organometallics,* 1998, 17, 5908–5912).

In light of these apparent deficiencies, it would be desirable to provide novel compounds having improved efficiency and operability as activators of metal complexes for olefin polymerizations.

SUMMARY OF THE INVENTION

According to the present invention there is now provided a compound corresponding to the formula: $AlAr^fQ^1Q^2$, or a dimer, adduct, or mixture thereof; where:

$Ar^f$ is a fluorinated aromatic hydrocarbyl moiety of from 6 to 30 carbon atoms;

$Q^1$ is $Ar^f$ or a $C_{1-20}$ hydrocarbyl group, optionally substituted with one or more cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally, such substituents may be covalently linked with each other to form one or more fused rings or ring systems; and $Q^2$ is an aryloxy, arylsulfide or di(hydrocarbyl)amido group, optionally substituted with one or more hydrocarbyl, cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally such substituents may be covalently linked with each other to form one or more fused rings or ring systems, said $Q^2$ having from 3 to 20 atoms other than hydrogen.

The subject invention further provides a method for preparing the foregoing compound comprising contacting under ligand exchange reaction conditions a trifluoroarylaluminum or trifluoroarylboron compound of the formula $Ar^f_3Me^1$,
wherein $Ar^f$ is as previously defined, and $Me^1$ is aluminum or boron,
with a Group 13 organometallic compound of the formula: $Q^3_2Me^2Q^2$, wherein $Q^2$ is as previously defined;

$Q^3$ is independently each occurrence $C_{1-4}$ alkyl; and $Me^2$ is a Group 13 metal, with the proviso that if $Me^1$ is boron, then $Me^2$ is aluminum.

In a particular embodiment of the foregoing method for preparing the compounds, a stoichiometric excess of the Group 13 organometallic compound of the formula: $Q^3_2Me^2Q^2$ is employed in the ligand exchange reaction. The resulting reaction mixture accordingly does not include significant quantities of residual trifluoroarylaluminum or trifluoroarylboron compound.

The subject invention further provides a catalyst composition for polymerization of olefins comprising a Group 3–10 metal complex and an activator comprising the above described compound or composition, the molar ratio of metal complex to activator in the catalyst composition being from 0.1:1 to 3:1.

The subject invention further provides a process for the polymerization of one or more addition polymerizable monomers comprising contacting one or more addition polymerizable monomers under addition polymerization conditions with the catalyst composition as described above.

These and other embodiments are more fully described in the following detailed description.

DETAILED DESCRIPTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups. The full teachings of any patent, patent application, provisional application, or publication referred to herein are hereby incorporated by reference.

Preferred compositions according to the present invention are those wherein Ar is a perfluoroaryl group, more preferably a perfluorophenyl group, $Q^1$ is $C_{3-6}$ alkyl containing at least one secondary or tertiary carbon center, more preferably isopropyl or isobutyl, and $Q^2$ is aryloxy or dialkylamido of up to 10 carbons, more preferably 2,6-di-(t-butyl) phenoxy, 2,6-di-(t-butyl)-4-methylphenoxy, N,N-bis (trimethylsilyl)amido, or N,N-dimethylamido. Most preferred compounds are monomers, rather than dimers or adducts.

In another preferred embodiment, the foregoing compounds are prochiral and optically inactive, however four coordinate derivatives thereof are chiral.

A most preferred aluminum compound formed according to the invention is isobutyl(perfluorophenyl)-2-methyl-4,6-di-(t-butyl)phenoxyaluminum or isobutyl(perfluorophenyl)-4,6-di-(t-butyl)phenoxyaluminum.

In a preferred process for making the compounds of the invention the exchange reaction is conducted in an aliphatic, cycloaliphatic or aromatic hydrocarbon liquid or mixture thereof under anhydrous conditions. Preferably, the Group 13 organometallic compound is an aluminum compound and is provided in a stoichiometric excess with respect to the trifluoroaryl aluminum or trifluoroaryl boron compound, more preferably at a molar ratio from 1:1 to 20:1, most preferably from 1:1 to 10:1. Preferred are the use of solutions of the foregoing reactants in concentrations of fluoroaryl compound and Group 13 compound from 0.005 to 2M, preferably from 0.02 to 1.5 M, and most preferably from 0.05 to 1.2 M. Generally, the Group 13 organometallic compound readily transfers one $Q^3$ group. However, the rate of transfer of a second $Q^3$ group is kinetically disfavored, thereby allowing for the recovery of the desired product in high yield and efficiency.

The rate of ligand exchange can be enhanced by heating the reaction mixture or by removing any alkyl exchange byproducts in the reaction mixture, especially any trialkylborane byproducts. A preferred temperature range for the exchange reaction is from 0 to 50° C., more preferably from 15 to 35° C. Suitable techniques for removing alkyl exchange byproducts from the reaction mixture include degassing optionally at reduced pressures, distillation, solvent exchange, solvent extraction, extraction with a volatile agent, contacting with a zeolite or molecular sieve, and combinations of the foregoing techniques, all of which are conducted according to conventional procedures. Purity of the resulting product may be determined by analysis of the reaction mixture. Desirably the content of trialkylboron compound in the compounds of the invention is less than 1 percent by weight, preferably less than 0.1 percent by weight. Removal of volatile by-products will assist in shifting the equilibrium concentration of desired end products. Generally, reaction times from 10 minutes to 6 hours, preferably 15 minutes to 1 hour are used to ensure formation of the desired ligand exchange products.

In as much as the present compounds are desirably prepared by an exchange reaction as previously described, it is to be understood that the resulting product mixture may include species in addition to those of the formula, $AlAr^fQ^1Q^2$. Additional components may include starting reactants as well as alternative exchange products. It is to be understood that the compounds of the invention may be prepared and used in the form of such a mixture of compounds. More particularly, alternative exchange products and starting reactants that may be found in such a mixture include compounds corresponding to the formula: $[Me^1Q^1{}_3]$ where:

$Q^1$ is $Ar^f$ or a $C_{1-20}$ hydrocarbyl group, optionally substituted with one or more cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally, such substituents may be covalently linked with each other to form one or more fused rings or ring systems;

$Ar^f$ is a fluorinated aromatic hydrocarbyl moiety of from 6 to 30 carbon atoms; and $Me^1$ is boron or aluminum, especially aluminum.

The exchange process is more particularly illustrated by reference to the following particular embodiment. (Isobutyl)(perfluorophenyl)(2-methyl-4,6-di-t-butylphenoxy)aluminum, which has been found to be an effective and useful cocatalyst for use in olefin polymerizations in combination with a group 4 metal complex, may be prepared by reacting tris(perfluorophenyl)borane (FAB) with diisobutyl-2,6-di-t-butyl-4-methylphenoxyaluminum (DIBAL-BOT) in a suitable diluent, preferably a hydrocarbon liquid. Preferably, the DIBAL-BOT is provided in stoichiometric excess with respect to the FAB. Further preferably, the two reagents are combined in solutions having concentrations of at least 0.005 M, preferably at least 0.05 M, more preferably at least 0.02 M; and, for reasons of solubility, typically no more than 2 M, preferably, no more than 1.5 M, and most preferably no more than 1.2 M. The use of excess Di-BAL-BOT insures the production of tri-coordinate aluminum species and likewise efficiently distributes all of the costly perfluoroaryl groups to aluminum, the co-product being mainly triisobutylboron, as illustrated in the following reaction scheme:

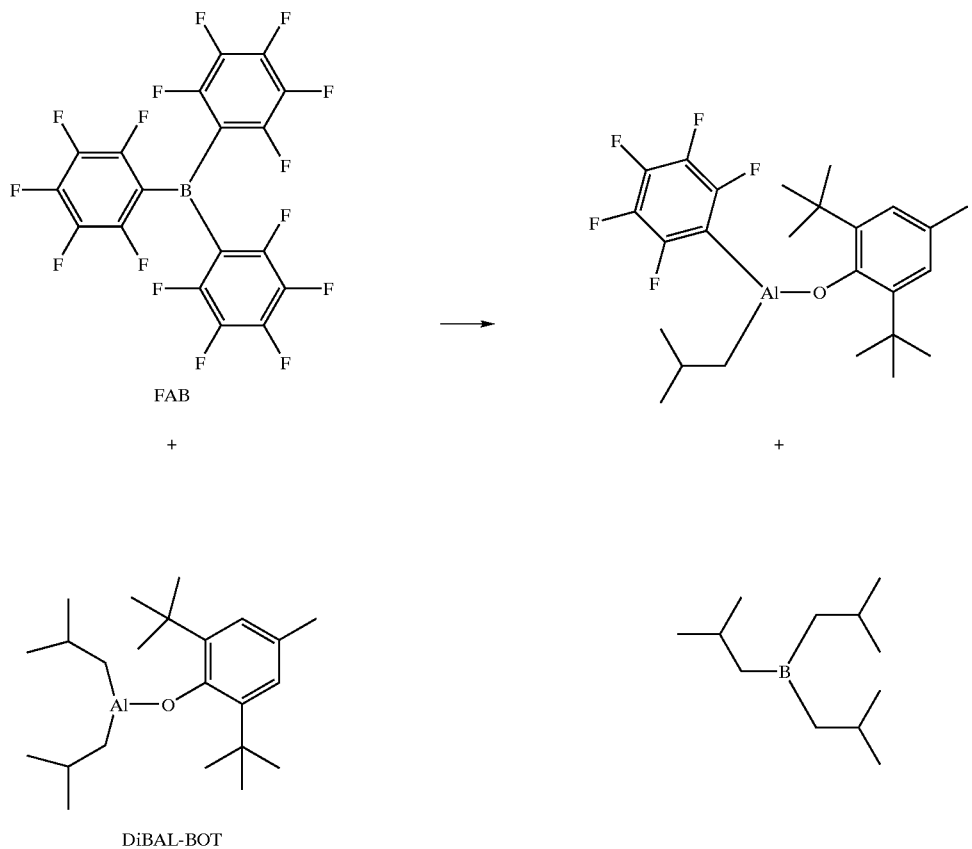

The rate of exchange reaction can be conveniently monitored by $^{19}F$ and $^1H$ NMR spectroscopy to ensure complete reaction.

In an alternate preferred embodiment of the invention, the activator isobutylperfluorophenyl-2-methyl-4,6-di-t-butylphenoxyaluminum, is prepared by reacting tris-(perfluorophenyl)aluminum (FAAL, which typically exists as a stoichiometric toluene solvate) with DiBAL-BOT in a hydrocarbon or aromatic solvent to produce the isobutylperfluorophenyl-2-methyl-4,6-di-t-butylphenoxyaluminum via an intermediate species, bis-perfluorophenylisobutylaluminum. This alternate embodiment of the invention is illustrated by the following reaction scheme:

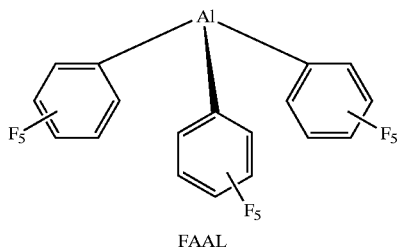

FAAL

+

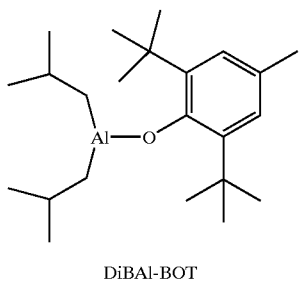

DiBAl-BOT

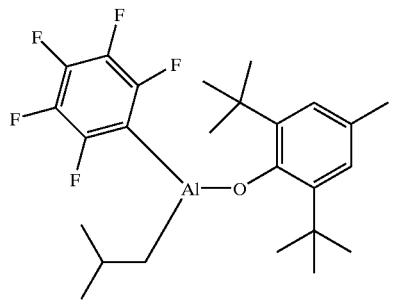

+

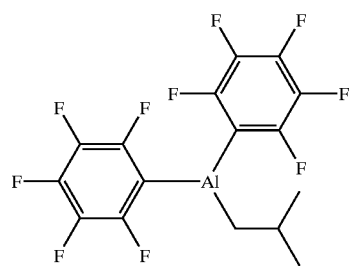

In this process, lower ratios of FAAL:DIBALBOT (1:1–1:2) form a highly active formulation, consisting of essentially two active aluminum components, bis-perfluorophenylisobutyl-aluminum and (perfluorophenyl) (isobutyl)(2-methyl-4,6-di-t-butylphenoxy)aluminum. It has now been determined that the partial exchange product, bis-perfluorophenylisobutylaluminum, is a highly active cocatalyst for use with group 4 metal complexes in an olefin polymerization. The use of higher ratios of DIBAL-BOT to FAAL (5–10:1) favors extinction of bisperfluorophenyl-isobutylaluminum and increases the amount of isobutylperfluorophenyl-2-methyl-4,6-di-t-butylphenoxyaluminum in the mixture. These ratios are not intended to limit the nature of the invention and may provide a suitable means for tailoring the efficiency of broad classes of metal complexes which may require a combination of these activators.

The present composition provides a highly active co-catalyst for use in activation of metal complexes, especially Group 4 metallocenes for the polymerization of olefins. In such use it is desirably employed as a dilute concentration in a hydrocarbon liquid, especially an aliphatic hydrocarbon liquid for use as a homogeneous catalyst, especially for solution polymerizations. Additionally, the composition may be deposited on an inert support, especially a particulated metal oxide or polymer, in combination with the metal complex to be activated according to known techniques for producing supported olefin polymerization catalysts, and thereafter used for gas phase or slurry polymerizations.

The present compounds and compositions provide highly active co-catalysts for use in activation of metal complexes, especially Group 4 metallocenes for the polymerization of olefins. In such use they are desirably employed as a dilute solution in a hydrocarbon liquid, especially an aliphatic hydrocarbon liquid for use as a homogeneous catalyst, especially for solution polymerizations. Additionally, the compound, or composition may be deposited on an inert support, especially a particulated metal oxide or polymer, in combination with the metal complex to be activated according to known techniques for producing supported olefin polymerization catalysts, and thereafter used for gas phase or slurry polymerizations.

When in use as a catalyst activator, the molar ratio of metal complex to activator composition is preferably from 0.1:1 to 3:1, more preferably from 0.2:1 to 2:1, most preferably from 0.25:1 to 1:1, based on the metal contents of each component. In most polymerization reactions the molar ratio of metal complex: polymerizable compound employed is from $10^{-12}:1$ to $10^{-1}:1$, more preferably from $10^{-12}:1$ to $10^{-5}:1$.

The support for the activator component may be any inert, particulate material, but most suitably is a metal oxide or mixture of metal oxides, preferably alumina, silica, an aluminosilicate or clay material. Suitable volume average particle sizes of the support are from 1 to 1000 $\mu$M, preferably from 10 to 100 $\mu$M. Most desired supports are calcined silica, which may be treated prior to use to reduce surface hydroxyl groups thereon, by reaction with a silane, a trialkylaluminum, or similar reactive compound. Any suitable means for incorporating the perfluoroaryl) aluminum co-catalyst mixture onto the surface of a support may be used, including dispersing the co-catalyst in a liquid and contacting the same with the support by slurrying, impregnation, spraying, or coating and thereafter removing the liquid, or by combining the cocatalyst and a support material in dry or paste form and intimately contacting the mixture, thereafter forming a dried, particulated product.

Suitable metal complexes for use in combination with the foregoing cocatalysts include any complex of a metal of Groups 3–10 of the Periodic table of the Elements capable of being activated to polymerize addition polymerizable compounds, especially olefins by the present activators.

Examples include Group 10 diimine derivatives corresponding to the formula:

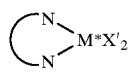

wherein

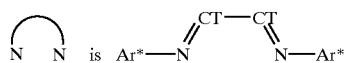

M* is Ni(II) or Pd(II);

X' is halo, hydrocarbyl, or hydrocarbyloxy;

Ar* is an aryl group, especially 2,6-diisopropylphenyl or aniline group; and

CT—CT is 1,2-ethanediyl, 2,3-butanediyl, or form a fused ring system wherein the two T groups together are a 1,8-naphthanediyl group.

Similar complexes to the foregoing are disclosed by M. Brookhart, et al., in *J. Am. Chem. Soc.*, 118, 267–268 (1996) and *J. Am. Chem. Soc.*, 117, 6414–6415 (1995), as being suitable for forming active polymerization catalysts especially for polymerization of α-olefins, either alone or in combination with polar comonomers such as vinyl chloride, alkyl acrylates and alkyl methacrylates.

Additional complexes include derivatives of Group 3, 4, or Lanthanide metals containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, phosphoyl groups and arene groups. By the term "π-bonded" is meant that the ligand group is bonded to the transition metal by a sharing of electrons from a delocalized π-bond.

Each atom in the delocalized 7u-bonded group may independently be substituted with a radical selected from the group consisting of hydrogen, halogen, hydrocarbyl, halohydrocarbyl, hydrocarbyloxy, hydrocarbylsulfide, dihydrocarbylamino, and hydrocarbyl-substituted metalloid radicals wherein the metalloid is selected from Group 14 of the Periodic Table of the Elements, and such hydrocarbyl-, halohydrocarbyl-, hydrocarbyloxy-, hydrocarbylsulfide-, dihydrocarbylamino- or hydrocarbyl-substituted metalloid-radicals that are further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyidimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, for example amide, phosphide, ether or thioether groups bonded to the transition metal or Lanthanide metal, and bonded to the hydrocarbyl group or to the hydrocarbyl-substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted, $C_{1-10}$ hydrocarbyloxy-substituted, di($C_{1-10}$ hydrocarbyl)amino-substituted, or tri($C_{1-10}$ hydrocarbyl) silyl-substituted derivatives thereof. Preferred anionic delocalized π-bonded groups are cyclopentadienyl, pentamethylcyclopentadienyl, tetramethylcyclopentadienyl, tetramethylsilylcyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 1995, 14, 1, 471–480. Preferred boratabenzenes correspond to the formula:

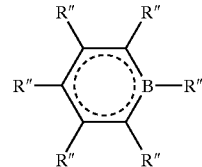

wherein R" is selected from the group consisting of hydrocarbyl, silyl, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

Suitable metal complexes for use in the catalysts of the present invention may be derivatives of any transition metal including Lanthanides, but preferably of Group 3, 4, or Lanthanide metals which are in the +2, +3, or +4 formal oxidation state meeting the previously mentioned requirements. Preferred compounds include metal complexes (metallocenes) containing from 1 to 3 π-bonded anionic ligand groups, which may be cyclic or noncyclic delocalized π-bonded anionic ligand groups. Exemplary of such π-bonded anionic ligand groups are conjugated or nonconjugated, cyclic or non-cyclic dienyl groups, allyl groups, and arene groups. By the term "π-bonded" is meant that the ligand group is bonded to the transition metal by means of delocalized electrons present in a π bond.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, and decahydroanthracenyl groups, as well as $C_{1-10}$ hydrocarbyl-substituted derivatives thereof. Preferred anionic delocalized π-bonded groups are cyclopentadienyl, pentamethylcyclopentadienyl, tetramethylcyclopentadienyl, indenyl, 2,3-dimethylindenyl, fluorenyl, 2-methylindenyl and 2-methyl-4-phenylindenyl.

More preferred are metal complexes corresponding to the formula:

$L_lMX_mX'_nX''_p$, or a dimer thereof wherein:
- L is an anionic, delocalized, π-bonded group that is bound to M, containing up to 50 atoms not counting hydrogen, optionally two L groups may be joined together through one or more substituents thereby forming a bridged structure, and further optionally one L may be bound to X through one or more substituents of L;
- M is a metal of Group 4 of the Periodic Table of the Elements in the +2, +3 or +4 formal oxidation state;
- X is an optional, divalent substituent of up to 50 non-hydrogen atoms that together with L forms a metallocycle with M;
- X' is an optional neutral Lewis base having up to 20 non-hydrogen atoms;
- X" each occurrence is a monovalent, anionic moiety having up to 40 non-hydrogen atoms, optionally, two X" groups may be covalently bound together forming a divalent dianionic moiety having both valences bound to M, or form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;
- l is 1 or 2;
- m is 0 or 1;
- n is a number from 0 to 3;
- p is an integer from 0 to 3; and
- the sum, l+m+p, is equal to the formal oxidation state of M.

Such preferred complexes include those containing either one or two L groups. The latter complexes include those containing a bridging group linking the two L groups. Preferred bridging groups are those corresponding to the formula $(ER^*_2)_x$ wherein E is silicon or carbon, $R^*$ independently each occurrence is hydrogen or a group selected from silyl, hydrocarbyl, hydrocarbyloxy and combinations thereof, said $R^*$ having up to 30 carbon or silicon atoms, and x is 1 to 8. Preferably, $R^*$ independently each occurrence is methyl, benzyl, tert-butyl or phenyl.

Examples of the foregoing bis(L) containing complexes are compounds corresponding to the formula:

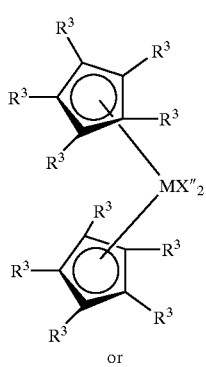

(I)

or

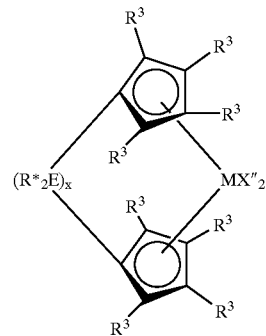

(II)

wherein:
- M is titanium, zirconium or hafnium, preferably zirconium or hafnium, in the +2 or +4 formal oxidation state;
- $R^3$ in each occurrence independently is selected from the group consisting of hydrogen, hydrocarbyl, dihydrocarbylamino, hydrocarbyleneamino, silyl, germyl, cyano, halo and combinations thereof, said $R^3$ having up to 20 atoms not counting hydrogen, or adjacent $R^3$ groups together form a divalent derivative thereby forming a fused ring system, and
- X" independently each occurrence is an anionic ligand group of up to 40 atoms not counting hydrogen, or two X" groups together form a divalent anionic ligand group of up to 40 atoms not counting hydrogen or together are a conjugated diene having from 4 to 30 atoms not counting hydrogen forming a π-complex with M, whereupon M is in the +2 formal oxidation state, and
- $R^*$, E and x are as previously defined.

The foregoing metal complexes are especially suited for the preparation of polymers having stereoregular molecular structure. In such capacity it is preferred that the complex possess $C_2$ symmetry or possess a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include bis-indenyl complexes. Similar systems based on Ti(IV) or Zr(IV) were disclosed for preparation of isotactic olefin polymers in Wild et al., *J. Organomet. Chem,* 232, 233–47, (1982).

Exemplary bridged ligands containing two π-bonded groups are: (dimethylsilyl-bis-cyclopentadienyl), (dimethylsilyl-bis-methylcyclopentadienyl), (dimethylsilyl-bis-ethylcyclopentadienyl, (dimethylsilyl-bis-t-butylcyclopentadienyl), (dimethylsilyl-bis-tetramethylcyclopentadienyl), (dimethylsilyl-bis-indenyl), (dimethylsilyl-bis-tetrahydroindenyl), (dimethylsilyl-bis-fluorenyl), (dimethylsilyl-bis-tetrahydrofluorenyl), (dimethylsilyl-bis-2-methyl-4-phenylindenyl), (dimethylsilyl-bis-2-methylindenyl), (dimethylsilyl-cyclopentadienyl-fluorenyl), (1,1,2,2-tetramethyl-1,2-disilyl-bis-cyclopentadienyl), (1,2-bis(cyclopentadienyl) ethane, and (isopropylidene-cyclopentadienyl-fluorenyl).

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention correspond to the formula:

$$L_lMX_mX'_nX''_p,\text{ or a dimer thereof}$$

wherein:
L is an anionic, delocalized, π-bonded group that is bound to M, containing up to 50 atoms not counting hydrogen;
M is a metal of Group 4 of the Periodic Table of the Elements in the +2, +3 or +4 formal oxidation state;
X is a divalent substituent of up to 50 non-hydrogen atoms that together with L forms a metallocycle with M;
X' is an optional neutral Lewis base ligand having up to 20 non-hydrogen atoms;
X" each occurrence is a monovalent, anionic moiety having up to 20 non-hydrogen atoms, optionally two X" groups together may form a divalent anionic moiety having both valences bound to M or a neutral $C_{5-30}$ conjugated diene, and further optionally X' and X" may be bonded together thereby forming a moiety that is both covalently bound to M and coordinated thereto by means of Lewis base functionality;
l is 1 or 2;
m is 1;
n is a number from 0 to 3;
p is an integer from 1 to 2; and
the sum, l+m+p, is equal to the formal oxidation state of M.

Preferred divalent X substituents preferably include groups containing up to 30 atoms not counting hydrogen and comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention correspond to the formula:

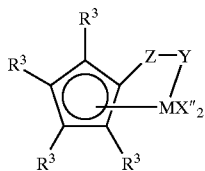

wherein:
M is titanium or zirconium in the +2 or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system,
each X" is a halo, hydrocarbyl, hydrocarbyloxy or silyl group, said group having up to 20 atoms not counting hydrogen, or two X" groups together form a $C_{5-30}$ conjugated diene;
Y is —O—, —S—, —NR*—, —PR*—; and
Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein: R* is as previously defined.

Illustrative Group 4 metal complexes that may be employed in the practice of the present invention include:
cyclopentadienyltitaniumtrimethyl,
cyclopentadienyltitaniumtriethyl,
cyclopentadienyltitaniumtriisopropyl,
cyclopentadienyltitaniumtriphenyl,
cyclopentadienyltitaniumtribenzyl,
cyclopentadienyltitanium-2,4-pentadienyl,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltitaniumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
($\eta^5$-2,4-dimethyl-1,3-pentadienyl)titaniumtrimethyl,
octahydrofluorenyltitaniumtrimethyl,
tetrahydroindenyltitaniumtrimethyl,
tetrahydrofluorenyltitaniumtrimethyl,
(1,1-dimethyl-2,3,4,9,10-η-1,4,5,6,7,8-hexahydronaphthalenyl)titaniumtrimethyl,
(1,1,2,3-tetramethyl-2,3,4,9,10-η-1,4,5,6,7,8-hexahydronaphthalenyl)titaniumtrimethyl,
(tert-butylamido)(tetramethyl-$\eta^5$-cyclopentadienyl) dimethylsilanetitanium dimethyl,
(tert-butylamido)(tetramethyl-$\eta^5$-cyclopentadienyl)-1,2-ethanediyltitanium dimethyl,
(tert-butylamido)(hexamethyl-$\eta^5$-indenyl) dimethylsilanetitanium dimethyl,
(tert-butylamido)(tetramethyl-$\eta^5$-cyclopentadienyl) dimethylsilane titanium (III) 2-(dimethylamino)benzyl;
(tert-butylamido)(tetramethyl-$\eta^5$-cyclopentadienyl) dimethylsilanetitanium (III) allyl,
(tert-butylamido)(tetramethyl-$\eta^5$-cyclopentadienyl) dimethylsilanetitanium (II) 1,4-diphenyl-1,3-butadiene,
(tert-butylamido)(2-methylindenyl)dimethylsilanetitanium (II) 1,4-diphenyl-1,3-butadiene,
(tert-butylamido)(2-methylindenyl)dimethylsilanetitanium (IV) 1,3-butadiene,
(tert-butylamido)(2,3-dimethylindenyl) dimethylsilanetitanium (II) 1,4-diphenyl-1,3-butadiene,
(tert-butylamido)(2,3-dimethylindenyl) dimethylsilanetitanium (IV) 1,3-butadiene,
(tert-butylamido)(2,3-dimethylindenyl) dimethylsilanetitanium (II)1,3-pentadiene,
(tert-butylamido)(2-methylindenyl)dimethylsilanetitanium (II) 1,3-pentadiene,
(tert-butylamido) (2-methylindenyl)dimethylsilanetitanium (IV) dimethyl,
(tert-butylamido) (2-methyl-4-phenylindenyl) dimethylsilanetitanium (II) 1,4-diphenyl-1,3-butadiene,
(tert-butylamido)(tetramethyl-$\eta^5$-cyclopentadienyl) dimethylsilanetitanium (IV) 1,3-butadiene,
(tert-butylamido)(tetramethyl-$\eta^5$-cyclopentadienyl) dimethylsilanetitanium (II ) 1,4-dibenzyl-1,3-butadiene,
(tert-butylamido)(tetramethyl-$\eta^5$-cyclopentadienyl) dimethylsilanetitanium (II) 2,4-hexadiene,
(tert-butylamido)(tetramethyl-$\eta^5$-cyclopentadienyl) dimethylsilanetitanium (II) 3-methyl 1,3-pentadiene,
(tert-butylamido)(2,4-dimethyl-1,3-pentadien-2-yl) dimethylsilanetitaniumdimethyl,
(tert-butylamido)(1,1-dimethyl-2,3,4,9,10-η-1,4,5,6,7,8-hexahydronaphthalen-4-yl) dimethylsilanetitaniumdimethyl, (tert-butylamido)(1,1,2,3-tetramethyl-2,3,4,9,10-η-1,4,5,6,
7,8-hexahydronaphthalen-4-yl)
dimethylsilanetitaniumdimethyl,
(tert-butylamido)(tetramethylcyclopentadienyl)
dimethylsilanetitanium 1,3-pentadiene,
(tert-butylamido)(3-(N-pyrrolidinyl)inden-1-yl)
dimethylsilanetitanium 1,3-pentadiene,
(tert-butylamido)(2-methyl-s-indacen-1-yl)
dimethylsilanetitanium 1,3-pentadiene, and (tert-butylamido)(3,4-cyclopenta(/)phenanthren-2-yl)
dimethylsilanetitanium 1,4-diphenyl-1,3-butadiene.

Bis(L) containing complexes including bridged complexes suitable for use in the present invention include:
biscyclopentadienylzirconiumdimethyl,
biscyclopentadienylzirconiumdiethyl,
biscyclopentadienylzirconiumdiisopropyl,
biscyclopentadienylzirconiumdiphenyl,
biscyclopentadienylzirconium dibenzyl,
biscyclopentadienylzirconium-2,4-pentadienyl,
biscyclopentadienylzirconiummethylmethoxide,
bispentamethylcyclopentadienylzirconiumdimethyl,
bisindenylzirconiumdimethyl,
indenylfluorenylzirconiumdiethyl,
bisindenylzirconiummethyl(2-(dimethylamino)benzyl),
bisindenylzirconium methyltrimethylsilyl,
bistetrahydroindenylzirconium methyltrimethylsilyl,
bispentamethylcyclopentadienylzirconiumdiisopropyl,
bispentamethylcyclopentadienylzirconiumdibenzyl,
bispentamethylcyclopentadienylzirconiummethylmethoxide,
(dimethylsilyl-bis-cyclopentadienyl)zirconiumdimethyl,
(dimethylsilyl-bis-pentamethylcyclopentadienyl)zirconium-
 2,4-pentadienyl,
(methylene-bis-pentamethylcyclopentadienyl)zirconium
 (III) 2-(dimethylamino)benzyl,
(dimethylsilyl-bis-2-methylindenyl)zirconiumdimethyl,
(dimethylsilyl-bis-2-methyl-4-phenylindenyl)
 zirconiumdimethyl,
(dimethylsilyl-bis-2-methylindenyl)zirconium-1,4-
 diphenyl-1,3-butadiene,
(dimethylsilyl-bis-2-methyl-4-phenylindenyl)zirconium(II)
 1,4-diphenyl-1,3-butadiene, (dimethylsilyl-bis-tetrahydroindenyl)zirconium(II) 1,4-diphenyl-1,3-butadiene,
(dimethylsilyl-bis-tetrahydrofluorenyl)zirconiumdi
 (trimethylsilyl),
(isopropylidene)(cyclopentadienyl)(fluorenyl)
 zirconiumdibenzyl, and
(dimethylsilylpentamethylcyclopentadienylfluorenyl)
 zirconiumdimethyl.

Suitable polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1,1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1, 1-hexene, 1-octene, and combinations of ethylene and/or propene with one or more of such other alpha-olefins. Other preferred monomers include styrene, halo- or alkyl substituted styrenes, tetrafluoroethylene, vinylcyclobutene, 1,4-hexadiene, dicyclopentadiene, ethylidene norbornene, and 1,7-octadiene. Mixtures of the above-mentioned monomers may also be employed.

In general, the polymerization may be accomplished at conditions well known in the prior art for solution phase, slurry, gas phase and high pressure Ziegler-Natta or Kaminsky-Sinn type polymerization reactions. Examples of such well known polymerization processes are depicted in WO 88/02009, U.S. Pat. Nos. 5,084,534, 5,405,922, 4,588, 790, 5,032,652, 4,543,399, 4,564,647, 4,522,987, and elsewhere. Preferred polymerization temperatures are from 0–250° C. Preferred polymerization pressures are from atmospheric to 3000 atmospheres. Molecular weight control agents can be used in combination with the present cocatalysts. Examples of such molecular weight control agents include hydrogen, silanes or other known chain transfer agents. The catalyst composition may be used by itself (homogeneously) or supported on an inert support such as silica, alumina or a polymer.

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. Where stated, the term "room temperature" refers to a temperature from 20 to 25° C., the term "overnight" refers to a time from 12 to 18 hours, and the term "mixed alkanes" refers to a mixture of propylene oligomers sold by Exxon Chemicals Inc. under the trade designation Isopar™ E.

EXAMPLES

Tris(perfluorophenyl)borane (FAB) was obtained as a solid from Boulder Scientific Inc. and used without further purification. Modified methalumoxane (MMAO-3A) in heptane was purchased from Akzo-Nobel. MAO and trimethylaluminum (TMA) both in toluene were purchased from Aldrich Chemical Co. Tris(perfluorophenyl)aluminum (FAAL) in toluene was prepared by exchange reaction between tris(perfluorophenyl)borane and trimethylaluminum. All solvents were purified using the technique disclosed by Pangborn et al, *Organometallics*, 1996, 15, 1518–1520. All compounds and solutions were handled under an inert atmosphere (dry box). All chemical shift for $^{19}F$ NMR spectra were relative to a fixed external standard ($CFCl_3$) in benzene $d_6$ or toluene $d_8$, either of which were dried over N/K alloy and filtered prior to use. $^1H$ and $^{13}C$ NMR shifts were referenced to internal solvent resonances and are reported relative to TMS.

Preparation of diisobutyl(2,6-di-t-butyl-4-methylphenoxy)aluminum (DIBAL-BOT) was conducted according to the method of Skowronska-Ptasinska, M. et al., *J. Organometallic Chem.*, 1978, 160, 403–409. The product was isolated as a colorless oil. NMR spectroscopic data are as follows: $^1H$ NMR ($C_6D_6$) δ7.08, 2.27(s,3H), 2.03, m, 1H, J=6.8 Hz), 1.48 (s, 18H), 1.02 (d, 12H, J=6.8 Hz), 0.39 (d, 12H, J=6.8 Hz); $^{13}C$ NMR ($C_6D_6$) δ153.9, 138.1, 127.2, 126.0, 34.8, 32.1, 28.2, 25.8, 24.0, 21.5. This product was used in the following ligand exchange reactions (Examples 1–5) to prepare isobutyl(pentafluorophenyl)(2,4-di-(t-butyl) 4-methylphenoxy)aluminum.

Example 1

In a glove box, FAAL (0.012 g, 0.02 mmol, toluene adduct) and DIBAL-BOT (0.007 g, 0.02 mmol) were mixed in 0.7 ml of benzene-$d_6$ and the mixture was loaded into a NMR tube. NMR spectra were recorded after mixing these reagents in the NMR tube for 10 min. Isobutyl (pentfluorophenyl)(2,4-di-(t-butyl)-4-methylphenoxy) aluminum was identified in the reaction mixture along with isobutylbis(pentafluorophenyl)aluminum. After 4 more hours at room temperature, no significant change in products or ratios of products was detected.

Spectroscopic data for di(isobutyl)(2,6-di-(t-butyl)-4-methylphenoxy)aluminum): $^1$H NMR ($C_6D_6$, 23° C.): δ7.10 (s, 2H, Ar), 2.25 (s, 3H, Ar—$CH_3$), 1.89 (septet, $J_{H-H}$=6.6 Hz, 1H, $Me_2CHCH_2$—),1.50 (s, 18H, tBu), 0.89 (d, $J_{H-H}$= 6.6 Hz, 6H, $Me_2CHCH_2$—), 0.50 (d, $J_{H-H}$=7.2Hz, 2H , $Me_2CHCH_2$—). $^{19}$F NMR ($C_6D_6$, 23° C.): δ–120.93 (dd, $^3J_{F-F}$=18.3 Hz, 2 F, o-F), –149.65 (t, $^3J_{F-F}$=21.4 Hz, 1 F, p-F), –159.61 (tt, $^3J_{F-F}$=24.5 Hz, 2F, m-F).

Example 2

The reaction conditions of Example 1 were substantially repeated using a molar ratio of FAAL to DIBAL-BOT of 1:3. Accordingly, in a glove box, FAAL (0.006 g, 0.01 mmol, toluene adduct) and DIBAL-BOT (0.011 g, 0.03 mmol) were mixed in 0.7 ml of benzene-$d_6$ and the mixture was loaded into a NMR tube. NMR spectra were recorded after mixing for 15 min. Isobutyl(pentafluorophenyl)(2,6-di-tert-butyl-4-methylphenoxy)aluminum and a minor amount of a dimer of isobutylbis(pentafluorophenyl)aluminum with diisobutyl(pentafluorophenyl)aluminum were found to form from the exchange. There was no FAAL reagent left in the reaction mixture. No significant change in product mix was detected after 4 h reaction.

Example 3

The reaction conditions of Example 1 were substantially repeated using FAB and DIBAL-BOT in a molar ratio of 1:3. Accordingly, in a glove box, FAB (0.01 g, 0.02 mmol) and DIBAL-BOT (0.022 g, 0.06 mmol) were mixed in 0.7 ml of benzene-$d_6$ and the mixture was loaded into a NMR tube. NMR spectra were recorded after mixing these reagents in the NMR tube for 30 min. Isobutylpentafluorophenyl(2,6-di-tert-butyl-4-methylphenoxy)aluminum along with quantities of diisobutylpentafluorophenylboron, triisobutylboron, and isobutyldi(2,6-tert-butyl-4-methylphenoxy) aluminum were found to form from the exchange. There was no FAB reagent left in the reaction mixture. After continued reaction for 12 h all diisobutylpentafluorophenylboron disappeared, giving a product mixture comprising triisobutylboron and isobutylpentafluorophenyl(2,6-di-(t-butyl)-4-methylphenoxy)aluminum.

/$BU_2B(C_6F_5)$ $^1$H NMR ($C_6D_6$, 23° C.): δ0.82 (d, $J_{H-H}$=6.6 Hz, 6H , $Me_2CHCH_2$—) and the rest of the resonances are overlapping with other species. $^{19}$F NMR ($C_6D_6$, 23° C.): δ–134.18 (dd, $^3J_{F-F}$=24.4 Hz, 2 F, o-F), –153.17 (t, $^3J_{F-F}$= 21.2 Hz, 1 F, p-F), –161.56 (tt, $^3J_{F-F}$=24.3 Hz, 2 F, m-F). /$Bu_3B$ $^1$H NMR ($C_6D_6$, 23° C.): δ0.92 (d, $J_{H-H}$=6.6 Hz, 6H, $Me_2CHCH_2$—) and the rest of the resonances are overlapping with other species.

Example 4

The reaction conditions of Example 3 were substantially repeated using FAB and DIBAL-BOT in a molar ratio of 1:10. Accordingly, in a glove box, FAB (0.005 g, 0.01 mmol) and DIBAL-BOT (0.036 g, 0.10 mmol) were mixed in 0.7 ml of benzene-$d_6$ and the mixture was loaded into a NMR tube. NMR spectra were recorded after mixing these reagents in the NMR tube for 15 min. The major identified species were isobutylpentafluorophenyl(2,6-di-(t-butyl)-4-methylphenoxy)aluminum and triisobutylboron, with smaller amounts of isobutyldi(2,6-di-(t-butyl)-4-methylphenoxy)aluminum and the dimer of isobutylbis (pentafluorophenyl)aluminum and diisobutylpentafluorophenylaluminum. There was no FAB reagent left in the reaction mixture.

Example 5

In a glove box, FAAL (0.012 g, 0.02 mmol, toluene adduct) and dimethyl(2,6-di(t-butyl)-4-methylphenoxy) aluminum (DIMAL-BOT) (0.006 g, 0.02 mmol) were mixed in 0.7 ml of benzene-$d_6$ and the mixture was loaded into a NMR tube. NMR spectra were recorded after mixing these reagents in the NMR tube for 1 h. An equilibrium mixture including starting compounds, methyl(pentafluorophenyl) (2,6-di(t-butyl)-4-methylphenoxy)aluminum, bis (pentafluorophenyl)(2,6-di(t-butyl)-4-methylphenoxy) aluminum the dimer of methyl(bispentafluorophenyl) aluminum and dimethylpentafluorophenylaluminum were identified.

Me($C_6F_5$)Al(BHT) $^1$H NMR ($C_6D_6$, 23° C.): δ7.10 (s, 2H, Ar), 2.25 (s, 3H, Ar—$CH_3$), 1.46 (s, 18H , tBu), –0.28 (s, 3H , MeAl). $^{19}$F NMR ($C_6D_6$, 23° C.): δ–121.29 (d, $^3J_{F-F}$=18.3 Hz, 2 F, o-F), –149.82 (t, $^3J_{F-F}$=21.4 Hz, 1 F, p-F), –159.99 (tt, $^3J_{F-F}$=24.5 Hz, 2 F, m-F). $C_6F_5)_2$Al(BHT) $^1$H NMR ($C_6D_6$, 23° C.): δ7.13 (s, 2H , Ar), 2.28 (s, 3H, Ar—$CH_3$), 1.52 (s, 18H , tBu). $^{19}$F NMR ($C_6D_6$, 23° C.): δ–121.06((dd, $^3J_{F-F}$=18.3 Hz, 2 F, o-F), –147.35 (t, $^3J_{F-F}$= 21.4 Hz, 1 F, p-F), –159.15 (tt, $^3J_{F-F}$=24.5 Hz, 2 F, m-F).

Polymerizations

A 2-liter Parr reactor was used in the polymerizations. All feeds were passed through columns of alumina and a decontaminant (Q-5 catalyst available from Englehardt Chemicals Inc.) prior to introduction into the reactor. Catalyst and cocatalysts are handled in a glovebox containing an atmosphere of argon or nitrogen.

A stirred 2.0 liter reactor is charged with about 740 g of mixed alkanes solvent and 118 g of 1-octene comonomer. Hydrogen is added as a molecular weight control agent by differential pressure expansion from a 75 ml addition tank at 25 psi (2070 kPa). The reactor is heated to the polymerization temperature of 130° C. and saturated with ethylene at 500 psig (3.4 MPa). FAAL or FAB are combined with diisobutyl(2,6-di-(t-butyl)-4-methylphenoxy)aluminum as toluene solutions and allowed to stand at 25° C. for 15 minutes prior to use. Catalyst (t-butylamido)dimethyl (tetramethylcyclopentadienyl)silanetitanium 1,3-pentadiene) and the indicated cocatalyst, as dilute solutions in toluene, are mixed at a ratio from 1:1 to 1:10, transferred to a catalyst addition tank, and injected into the reactor. The polymerization conditions are maintained for 15 minutes with ethylene added on demand. The resulting solution is removed from the reactor, quenched with isopropanol and stabilized by addition of 10 ml of a toluene solution containing approximately 67 mg of a hindered phenol antioxidant (Irganox™ 1010 from Ciba Geigy Corporation) and 133 mg of a phosphorus stabilizer (Irgafos™ 168 from Ciba Geigy Corporation.

Between polymerization runs a wash cycle in which 850 g of mixed alkanes is added to the reactor and the reactor heated to 150° C. The reactor is emptied of the heated solvent immediately before beginning a new polymerization run.

Polymers are recovered by drying in a vacuum oven set at 140° C. for about 20 hours. Density values are derived by determining the polymer's mass when in air and when immersed in methylethylketone. Micro melt index values (MMI) are obtained using a "Custom Scientific Instrument Inc. Model CS-127MF-015" apparatus at 190° C. MMI (micro-melt index) are unit-less values calculated as follows: MMI=1/(0.00343 t −0.00251), where t=time in seconds. Results are contained in Table 1.

TABLE 1

| Run | Activator(s) | μmoles catalyst/ activator** | Exotherm (° C.) | Yield (g) | Efficiency g polymer/μg Ti | Density g/ml | MMI |
|---|---|---|---|---|---|---|---|
| 1 | FAAL/Dibal-Bot | 0.75/3/15 | 1.4 | 20.9 | 0.58 | 0.904 | 0.5 |
| 2 | FAAL/Dibal-Bot | 1/4/8 | 1.9 | 25.4 | 0.53 | 0.904 | 0.5 |
| 3 | FAAL/Dibal-Bot | 0.75/3/3 | 5.2 | 68.6 | 1.91 | 0.905 | 1.2 |
| 4 | FAB/Dibal-Bot | 1/1/10 | 2.6 | 53.0 | 1.11 | 0.901 | 3.7 |
| A* | FAB | 1.5/1.5 | 1.3 | 48.7 | 0.68 | 0.901 | 9.3 |
| B* | FAAL | 0.5/0.5 | 0.0 | 0.9 | 0.038 | — | — |
| C* | FAAL | 0.25/1 | 1.3 | 0.1 | — | — | — |

*comparative example, not an example of the invention.
**Catalyst ratios reflect metal complex: first activator:second activator Popylene Homopolymerization The above polymerization conditions were substantially repeated excepting the 250 g of mixed alkanes solvent and 300 g of propylene are polymerized at a polymerization temperature of 70° C.

The cocatalyst was prepared by combining FAB with diisobutyl(2,6-di-(t-butyl)-4-methylphenoxy)aluminum in a molar ratio of 1:10 and allowing the mixture to stand at 25° C. for 15 minutes. The mixture was not devolatilized to remove triisopropylborane byproducts. Catalyst, dimethylsilanebis(2-methyl-4-phenylindenyl)zirconium 1,4-diphenyl-1,3-butadiene (1.0 μmole) and the indicated cocatalyst, as dilute solutions in toluene, are then mixed at a ratio from 1:1:10 (zirconium complex: FAB: DIBAL-BOT), transferred to a catalyst addition tank, and injected into the reactor. The polymerization conditions are maintained for 15 minutes. The resulting solution is removed from the reactor, quenched with isopropyl alcohol, and stabilized by addition of 10 ml of a toluene solution containing approximately 67 mg of a hindered phenol antioxidant (Irganox™ from Ciba Geigy Corporation) and 133 mg of a phosphorus stabilizer (Irgafos 168 Ciba Geigy Corporation). 63.2 g of isotactic polypropylene having Tm of 156° C., Mw=250,000, a molecular weight distribution (Mw/Mn) of 2.05 are recovered. Catalyst efficiency is 0.7 Kg/mg Zr.

What is claimed is:

1. A catalyst composition comprising a Group 3–10 metal complex and an activator compound corresponding to the formula: $AlAr^f Q^1 Q^2$; where:

$Ar^f$ is a fluorinated aromatic hydrocarbyl moiety of from 6 to 30 carbon atoms;

$Q^1$ is $Ar^f$ or a $C_{1-20}$ hydrocarbyl group, or a $C_{1-20}$ hydrocarbyl group substituted with one or more cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or such substituent groups may be covalently linked with each other to form one or more fused rings or ring systems; and $Q^2$ is an aryloxy, arylsulfideo or di(hydrocarbyl)amido group, or such group substituted with one or more hydrocarbyl, cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or such substituent groups may be covalently linked with each other to form one or more fused rings or ring systems, said $Q^2$ having from 3 to 20 atoms other than hydrogen.

2. A composition according to claim 1 wherein $Ar^f$ each occurrence is perfluorophenyl.

3. A composition according to claim 1 wherein $Ar^f$ is pentafluorophenyl, $Q^1$ is isobutyl, and $Q^2$ is 2,6-di-(t-butyl) phenoxy, 2,6-di-(t-butyl)-4-methylphenoxy, N,N-bis (trimethylsilyl)amido, or N,N-dimethylamido.

4. A composition according to claim 1 wherein $Ar^f$ is pentafluorophenyl, $Q^1$ is isobutyl, and $Q^2$ is 4-methyl-2,6-di-t-butylphenoxy.

5. A composition of any of claims 1–4 wherein the metal complex is a Group 4 metal complex.

6. The composition of claim 5 wherein the molar ratio of metal complex to activator compound is from 0.1:1 to 2:1.

7. The composition of claim 5 additionally comprising a support material in the form of a particulated solid.

8. The composition of claim 5 wherein the metal complex is:

(tert-butylamido)(tetramethylcyclopentadienyl) dimethylsilanetitanium dimethyl, (tert-butylamido)(tetramethylcyclopentadienyl) dimethylsilanetitanium 1,3-pentadiene, (tert-butylamido)(2-methyl-s-indacen-1-yl) dimethylsilanetitanium 1,3-pentadiene, (tert-butylamido)(3-(N-pyrrolidinyl)inden-1-yl) dimethylsilanetitanium 1,3-pentadiene, (tert-butylamido)(3,4-cyclopenta(l)phenanthren-2-yl) dimethylsilanetitanium 1,4-diphenyl-1,3-butadiene, (dimethylsilyl-bis-2-methyl-4-phenylindenyl)zirconium dimethyl, (dimethylsilyl-bis-2-methyl-4-phenylindenyl)zirconium 1,4-diphenyl-1,3-butadiene, (1,2-ethanediyl)bis(inden-1-yl)zirconium dimethyl, or (1,2-ethanediyl)bis(inden-1-yl)zirconium 1,4-diphenyl-1,3-butadiene.

* * * * *